(12) United States Patent
Peng et al.

(10) Patent No.: US 7,105,051 B2
(45) Date of Patent: Sep. 12, 2006

(54) HIGH QUALITY COLLOIDAL NANOCRYSTALS AND METHODS OF PREPARING THE SAME IN NON-COORDINATING SOLVENTS

(75) Inventors: Xiaogang Peng, Fayetteville, AR (US); Weiyong Yu, Fayetteville, AR (US); David Battaglia, Fayetteville, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 191 days.

(21) Appl. No.: 10/209,329

(22) Filed: Jul. 30, 2002

(65) Prior Publication Data

US 2006/0130741 A1    Jun. 22, 2006

Related U.S. Application Data

(60) Provisional application No. 60/308,689, filed on Jul. 30, 2001.

(51) Int. Cl.
*C30B 25/12* (2006.01)
(52) U.S. Cl. ............... 117/68; 117/11; 977/DIG. 1
(58) Field of Classification Search ............ 117/11, 117/68; 977/DIG. 1
See application file for complete search history.

(56) References Cited

U.S. PATENT DOCUMENTS

| | | | |
|---|---|---|---|
| 5,505,928 A | 4/1996 | Alivisatos et al. | |
| 5,559,057 A | 9/1996 | Goldstein | |
| 6,136,156 A * | 10/2000 | El-Shall et al. | 204/157.41 |
| 6,623,559 B1 * | 9/2003 | Huang | 117/87 |
| 6,645,444 B1 * | 11/2003 | Goldstein | 423/1 |
| 2003/0097976 A1 * | 5/2003 | Zehnder et al. | 117/68 |

OTHER PUBLICATIONS

Examiner STN Database Search, 24 Abstracts, Dec. 10, 2004.*
Artemyev, Mikhail V., et al., "Light Trapped in a Photonic Dot: Microspheres Act as a Cavity for Quantum Dot Emission," *Nano Letters*, vol. 1, No. 6, 2001, pp. 309-314.
Brennan, J.G., et al., "Bulk and Nanostructure Group II-VI Compounds from Molecular Organometallic Precursors," *Chem. Mater.*, vol. 2, No. 4, 1990, pp. 403-409.
Bruchez Jr., Marcel, et al., "Semiconductor Nanocrystals as Fluorescent Biological Labels," *Science*, vol. 281, Sep. 25, 1998, pp. 2013-2016.
Chan, Warren C. W., et al., "Quantum Dot Bioconjugates for Ultrasensitive Nonisotopic Detection," *Science*, vol. 281, Sep. 25, 1998, pp. 2016-2018.
Cumberland, Scott L., et al., "Inorganic Clusters as Single-Source Precursors for Preparation of CdSe, ZnSe, and CdSe/ZnS Nanomaterials," *Chem. Mater.*, vol. 14, No. 4, 2002, pp. 1576-1584.
Dabbousi, B.O., et al., "(CdSe)ZnS Core-Shell Quantum Dots: Synthesis and Characterization of a Size Series of Highly Luminescent Nanocrystallites," *J. Phys. Chem. B*, vol. 101, No. 46, 1997, pp. 9463-9475.

(Continued)

*Primary Examiner*—Felisa Hiteshew
(74) *Attorney, Agent, or Firm*—Kilpatrick Stockton LLP; J. Clinton Wimbish

(57) ABSTRACT

The present invention provides substantially monodisperse colloidal nanocrystals and new preparative methods for the synthesis of substantially monodisperse colloidal nanocrystals. These synthetic methods afford the ability to tune nanocrystal size and size distribution. By using non-coordinating solvents in the synthetic process, these procedures constitute easier, less expensive, safer, and more environmentally "green" methods than those currently in use. This invention is generally applicable to any II–VI or III–V semiconductor material, and may be useful in generating metal-nonmetal compounds involving transition metals as well.

29 Claims, 10 Drawing Sheets

OTHER PUBLICATIONS

Hines, Margaret A., et al., "Bright UV-Blue Luminescent Colloidal ZnSe Nanocrystals," *J. Phys. Chem. B*, vol. 102, No. 19, 1998, pp. 3655-3657.

Hines, Margaret A., et al., "Synthesis and Characterization of Strongly Luminescing ZnS-Capped CdSe Nanocrystals," *J. Phys. Chem.*, vol. 100, No. 2, 1996, pp. 468-471.

Hoheisel, W., et al., "Threshold for quasicontinuum absorption and reduced luminescence efficiency in CdSe nanocrystals," *J. Chem. Phys.*, vol. 101, No. 10, 1994, pp. 8455-8460.

Jun, Young-wook, et al., "Controlled Synthesis of Multi-armed CdS Nanorod Architectures Using Monosurfactant System," *J. Am. Chem. Soc.*, vol. 123, No. 21, 2001, pp. 5150-5151.

Klimov, V. I., et al., "Optical Gain and Stimulated Emission in Nanocrystal Quantum Dots," *Science*, vol. 290, Oct. 13, 2000, pp. 314-317.

Labella, V. P., et al., "Atomic Structure of the GaAs(001)-(2 × 4) Surface Resolved Using Scanning Tunneling Microscopy and First-Principles Theory," *Physical Review Letters*, vol. 83, No. 15, Oct. 11, 1999, pp. 2989-2992.

Lee, Jinwook, et al., "Full Color Emission from II-VI Semiconductor Quantum Dot-Polymer Composites" *Adv. Mater.*, vol. 12, No. 15, Aug. 2, 2000, pp. 1102-1105.

Lemon, Buford I., et al., "Preparation and Characterization of Dendrimer-Encapsulated CdS Semiconductor Quantum Dots," *J. Am. Chem. Soc.*, vol. 122, No. 51, 2000, pp. 12886-12887.

Murray, C.B., et al., "Synthesis and Characterization of Nearly Monodisperse CdE (E = S, Se, Te) Semiconductor Nanocrystallites," *J. Am. Chem. Soc.*, vol. 115, 1993, pp. 8706-8715.

Norris, D.J., et al., "High-Quality Manganese-Doped ZnSe Nanocrystals," *Nano Letters*, vol. 1, No. 1, 2001, pp. 3-7.

Peng, Xiaogang, et al., "Epitaxial Growth of Highly Luminescent CdSe/CdS Core/Shell Nanocrystals with Photostability and Electronic Accessibility," *J. Am. Chem. Soc.*, vol. 119, No. 30, 1997, pp. 7019-7029.

Peng, Xiaogang, et al., "Kinetics of II-VI and III-V Colloidal Semiconductor Nanocrystal Growth: 'Focusing of Size Distributions," *J. Am. Chem. Soc.*, vol. 120, No. 21, 1998, pp. 5343-5344.

Peng, Xiaogang, et al., "Shape control of CdSe nanocrystals," *Nature*, vol. 404, Mar. 2, 2000, pp. 59-61.

Peng, Z. Adam, et al., "Formation of High-Quality CdTe, CdSe, and CdS Nanocrystals Using CdO as Precursor," *J. Am. Chem. Soc.*, vol. 123, No. 1, 2001, pp. 183-184.

Peng, Z. Adam, et al., "Mechanisms of the Shape Evolution of CdSe Nanocrystals," *J. Am. Chem. Soc.*, vol. 123, No. 7, 2001, pp. 1389-1395.

Pickett, Nigel L., et al., "Syntheses of Semiconductor Nanoparticles Using Single-Molecular Precursors," *The Chemical Record*, vol. 1, 2001, pp. 467-479.

Talapin, Dmitri V., et al., "Highly Luminescent Monodisperse CdSe and CdSe/ZnS Nanocrystals Synthesized in a Hexadecylamine-Trioctylphosphine Mixture," *Nano Letters*, vol. 1, No. 4, 2001, pp. 207-211.

Qu, Lianhue, et al., "Alternative Routes toward High Quality CdSe Nanocrystals," *Nano Letters*, vol. 1, No. 6, 2001, pp. 333-337.

Vossmeyer, T., et al., "CdS Nanoclusters: Synthesis, Characterization, Size Dependent Oscillator Strength, Temperature Shift of the Excitonic Transition Energy, and Reversible Absorbance Shift," *J. Phys. Chem*, vol. 98, No. 13, 1994, pp. 7665-7673.

\* cited by examiner

HIGH QUALITY COLLOIDAL NANOCRYSTALS AND METHODS OF PREPARING THE SAME IN NON-COORDINATING SOLVENTS

PRIOR RELATED U.S. APPLICATION DATA

This application claims priority to U.S. provisional application Ser. No. 60/308,689, filed Jul. 30, 2001.

STATEMENT OF GOVERNMENT LICENSE RIGHTS

This invention was made through the support of the National Science Foundation (Grant No. CHE0101178). The Federal Government may retain certain license rights in this invention.

TECHNICAL FIELD OF THE INVENTION

The present invention provides new compositions containing colloidal nanocrystals in which the as-prepared nanocrystals are substantially monodiserse, and hiving high photoluminescence quantum yields. This invention also encompasses new synthetic method for the synthesis of substantially monodisperse colloidal nanocrystals using new preparative methods that afford tunable crystal size, shape, and size/shape distribution. By using non-coordinating solvents in the synthetic process, these procedures constitute easier, less expensive, safer, and more environmentally "green" methods than those currently in use. This invention is generally applicable to any II–VI or III–V semiconductor material, and should be useful in generating metal, and nonmetal compounds as well. The advantages of the use of non-coordinating solvents are demonstrated herein using semiconductor nanocrystals as the examples.

BACKGROUND OF THE INVENTION

High quality colloidal nanocrystals are nanometer sized fragments formed in solution with well-controlled size, shape, surface structures, and excellent chemical processibility. As used herein, chemical processibility means that nanocrystals can be treated as solution species. Colloidal nanocrystals are of great interest for industrial applications and academic studies because of their unique size dependent properties and flexible processing chemistry.

Colloidal nanocrystals, particularly of semiconductor materials, continue to exhibit tremendous promise for developing advanced materials, and have attracted great interest for their utility in fundamental research. These nanocrystal-based emitters can be used for many purposes, such as light-emitting diodes, lasers, biomedical tags, photoelectric devices, solar cells, catalysts, and the like. However, the lack of adequate synthetic methods for preparing high quality nanocrystals has hampered progress in this area, and delayed the timely development of advanced applications for these unique materials. Present synthetic schemes for semiconductor nanocrystals, including various organometallic approaches and their inorganic alternatives, are sometimes irreproducible and often provide crystals that are low in quality, possess high polydispersities, and may be plagued by impurities.

Many current preparative methods require the use of toxic, pyrophoric, and unstable reagents. For example, the synthesis of CdSe nanocrystals using dimethyl cadmium $(Cd(CH_3)_2)$ as the cadmium precursor is now well developed (Murray et al., J. Am. Chem. Soc. 1993, 115, 8706–8715; Barbera-Guillem, et al., U.S. Pat. No. 6,179,912; Peng et al., Nature 2000, 404, 69–61; Peng et al., J. Am. Chem. Soc. 1998, 120, 5343–5344). However, dimethyl cadmium is extremely toxic, pyrophoric, expensive, and unstable at room temperature. At the typical injection temperatures (340–360° C.) required for nanocrystal synthesis using $Cd(CH_3)_2$ as the precursor, $Cd(CH_3)_2$ is explosive by releasing large amounts of gas. For these reasons, the $Cd(CH_3)_2$ related synthesis methods require very restrictive equipment and conditions and, thus, are not ideal for large-scale synthesis.

Another limitation in current preparative methods for nanocrystals is their general inability to provide monodisperse samples. Currently, CdSe is the only compound for which nanocrystals having a relatively monodisperse size distribution can be directly synthesized (Peng, et al., J. Am. Chem. Soc. 1998, 120, 10, 5343–5344). Peng, et al. reported that the size distribution of CdSe nanocrystals can approach monodispersity (polydispersity index, PDI≈1), by controlling the monomer concentration in the initial reaction solution, and that CdSe nanocrystal size could be controlled by adjusting the time for crystal growth. There, thus, remains a need to develop a more generally applicable method for synthesizing high-quality semiconductor nanocrystals, whereby the size and size distribution of the nanocrystals can be well controlled during the growth stage ("focusing" of the size distribution).

Recently, Peng reported that the formation of high quality CdSe nanocrystals can be achieved by the use of stable, inexpensive, and safe inorganic cadmium salts, instead of dimethylcadmium (Peng, et al., J. Am. Chem. Soc., 2001, 123, 168; 2002, 124, 3343; Qu, et al., Nanoletters, 2001, 1, 333; J. Am. Chem. Soc., 2002, 124, 2049; U.S. patent application Ser. No. 09/971,780; U.S. Provisional Patent Application No. 60/275,008). However, the synthesis was performed in coordinating solvents, which resulted in limited success for the growth of high quality CdTe and CdS nanocrystals (Peng, et al., J. Am. Chem. Soc., 2001, 123, 168).

Current synthetic methods for high quality semiconductor nanocrystals, as discussed above, are exclusively performed in coordinating solvents, based upon the general belief that such solvents are necessary to adequately dissolve and allow complete reaction of their synthetic precursors. However, while long thought necessary, coordinating solvents suffer from several limitations as reaction media for synthesizing semiconductor nanocrystals. For example, the coordinating ability of representative solvents is often limited, making it very difficult to identify a good solvent system for a specific synthesis. Likely, this feature has limited the quality of available CdSe nanocrystals for many years. Further, coordinating solvents are often quite expensive, which may hinder large scale development efforts of an otherwise acceptable synthetic method. Many common coordinating solvents are toxic, and safety considerations may effectively preclude large scale syntheses. Thus, simply identifying a coordinating solvent with the necessary physical properties can be quite involved, thereby complicating the search for a suitable reaction system for growing high quality nanocrystals for most semiconductor materials.

Attempts to address these limitations have led to the general practice of using a mixture of several coordinating reagents as solvent. However, this practice also presents the non-trivial challenge of identifying an appropriate solvent system for crystal growth. Further, mixed solvent systems make it very difficult to identify the role of each component of the coordinating solvent in the growth of nanocrystals, which places further developments in this area on a highly empirical, rather than a more rational, basis. Moreover, such complicated reaction systems preclude so-called "green" chemical syntheses, because of the difficulty in recycling the raw materials and the toxicity of the most popular coordinating solvents, such as organophosphorus compounds.

Therefore, what is needed is an improved method to prepare semiconductor materials that affords high quality and pure nanocrystals. This method would also avoid the toxic solvents commonly used, and provide more green approaches to these nanocrystals using more recyclable solvents. Prefereably, the improved method would be amenable to syntheses in the air, rather than requiring an inert atmosphere, and it would use solvents that are liquid at room temperature to provide lower costs relative to current methods. If possible, the new method would also impart the ability to control the size of the nanocrystals produced, without sacrificing the desired narrow size distribution.

The present invention demonstrates that, despite the general belief that coordinating solvents are necessary for preparing semiconductor nanocrystals, these materials may in fact be prepared in non-coordinating solvents. Therefore, this invention exhibits the desired features described above by providing synthetic methods that produce high quality, small, and highly monodisperse semiconductor nanocrystals.

SUMMARY OF THE INVENTION

The present invention addresses the current limitations in the availability of high-quality colloidal nanocrystals by providing colloidal nanocrystals that, in their as-prepared state, luminesce between about 500–700 nm (inclusive), are highly monodisperse. The high monodispersity that can be achieved in this invention is seen in the photoluminescence emission line of the nanocrystals, which can have a full width at half maximum (FWHM) as narrow as 23–24 nm, with typical FWHM values of around 18–25 nm. The as-prepared nanocrystals described herein are further characterized by the photoluminescence quantum yield (PL QY) of up to about 60%. As-prepared nanocrystals ranging in size from about 1–6 nm in average diameter are typical, with the size range of these nanocrystals being very monodisperse, with 4–5 nm sizes being commonly prepared. Further, this invention encompasses new products and devices incorporating these nanocrystals, such as light-emitting diodes, biological labeling agent such as biomedical tags, photoelectric devices including solar cells, catalysts, lasers, and the like. As understood by one of ordinary skill in the art, prior nanocrystal syntheses typically require additional processing or size sorting steps after crystallization to achieve the desired size, size distribution, and other properties of the sample. The present invention affords improved sizes, size distributions, photoluminescence quantum yields, and related physical and chemical properties for colloidal nanocrystals in their "as-prepared" state, without the need for size sorting or further processing steps.

The present invention further addresses the current limitations in synthesizing monodisperse semiconductor nanocrystals by establishing that coordinating solvents are not intrinsically required for the synthesis of high quality semiconductor nanocrystals. This concept is used to develop new synthetic methods that afford, very selectively, tunable crystal sizes/shapes and size/shape distributions. Additionally, the use of non-coordinating solvents allows more environmentally innocuous precursors and ligands to be employed.

Thus, this new and reproducible synthetic method is significantly "greener" and less expensive than the existing schemes since the typical organophosphine/organophosphine oxide coordinating solvents are supplanted by non-coordinating solvents such as octadecene (ODE).

In its simplest form, one embodiment of this invention involves a method of synthesizing semiconductor nanocrystals by combining a cation precursor, a ligand, and a non-coordinating solvent to form a cation-ligand complex and then admixing an anion precursor dissolved in a non-coordinating solvent with the cation-ligand complex at a temperature sufficient to form nanocrystals. The cation precursors can be elements, covalent compounds, or ionic compounds, including coordination complexes or a metal salt, that serve as a source for the electropositive element or elements in the resulting nanocrystal. When feasible, inexpensive and safe compounds such as metal oxides are preferred. Anion precursors can also be elements, covalent compounds, or ionic compounds that serve as a source for the electronegative element or elements in the resulting nanocrystal. Inexpensive and safe compounds, such as naturally occurring substances, also constitute the preferred anion precursors. These definitions anticipate that ternary compounds, quaternary compounds, and even more complex species may be prepared using the methods disclosed herein, in which case more than one cation precursor and/or more than one anion precursor are typically required.

Generally, the methods disclosed herein are applicable to nanocrystals prepared using cation precursor compounds of the group II metals (for example, Zn, Cd or Hg), the group III metals (for example, Al, Ga, or In), the group IV metals (for example, Ge, Sn or Pb), or the transition metals (for example, Ti, Zr, Hf, V, Nb, Ta, Cr, Mo, W, Mn, Tc, Re, Fe, Co, Ni, Pd, Pt, Rh, and the like). (See, F. A. Cotton et al., Advanced Inorganic Chemistry, 6th Edition, (1999).) Further, the cation precursor can constitute a wide range of substances, such as a metal oxide, a metal carbonate, a metal bicarbonate, a metal sulfate, a metal sulfite, a metal phosphate, metal phosphite, a metal halide, a metal carboxylate, a metal alkoxide, a metal thiolate, a metal amide, a metal imide, a metal alkyl, a metal aryl, a metal coordination complex, a metal solvate, a metal salt, and the like. In a typical preparation, the ligand is selected from fatty acids, amines, phosphines, phosphine oxides, or phosphonic acids. Anion precursors are most often selected from the element itself (oxidation state 0), covalent compounds, or ionic compounds of the group V elements (N, P, As, or Sb), the group VI elements (O, S, Se or Te), the group VII elements (F, Cl, Br, or I).

In one embodiment of this invention, highly monodisperse CdS nanocrystals may be prepared by dissolving the cation precursor CdO in the non-coordinating solvent octadecene (ODE) through its reaction with oleic acid (OA; $C_{18}H_{34}O_2$) at elevated temperatures. The CdO, OA, ODE mixture was maintained at around 300° C., while a solution of the anion precursor, elemental sulfur in ODE, was swiftly injected into the hot solution. This hot mixture was then allowed to cool to about 250° C. to allow the growth of the CdS nanocrystals. This readily reproducible preparation can be carried out either under argon or open to air.

In another embodiment of this invention, nearly monodisperse InP nanocrystals may be prepared by dissolving cation precursor $In(Ac)_3$ (Ac=acetate, $O_2CCH_3$) in non-coordinating ODE solvent, through its reaction with various fatty acids at elevated temperatures. A sample of the anion precursor $P(TMS)_3$ (TMS=Si(CH_3)_3) dissolved in ODE under an inert atmosphere was injected into the hot In/ligand/ODE solution, and the temperature was subsequently lowered to grow monodisperse InP nanocrystals. This method works much better under an inert atmosphere, where exposure to air is substantially precluded. This reaction and crystallization scheme is of particular strategic importance in advancing the synthetic chemistry of the poorly developed III–V nanocrystal systems, which will further promote the industrial applications of these materials.

In another embodiment of this invention, nearly monodisperse CdTe nanocrystals may be prepared by dissolving CdO in ODE through its reaction with oleic acid (OA) at elevated temperatures. The CdO, OA, ODE mixture was maintained at around 270–300° C., while a solution of the anion precursor, elemental tellurium reacted with trihexylphosphine (THP) with a Te:THP molar ratio as about 1:1.1 in ODE, was swiftly injected into the hot solution. This hot mixture was then allowed to cool to about 250° C. to allow the growth of the CdTe nanocrystals. This readily reproducible preparation can be carried out under argon. The shape of the as-prepared CdTe nanocrystals can be tuned between mondisperse dots, rods, and branched shapes by varying the ligands.

In another embodiment of this invention, nearly monodisperse CdSe nanocrystals may be prepared by dissolving CdO in ODE through its reaction with stearic acid (SA) at elevated temperatures. The CdO, SA, ODE mixture was cooled down to room temperature and hexadecylamine (HDA) was added into the mixture as a co-ligand. The reaction mixture was consequently heated up to and maintained at around 270–300° C., while a solution of the anion precursor, elemental selenium reacted with tributylphosphine (TBP) with a Se:TBP molar ratio as about 1:1.1 in ODE, was swiftly injected into the hot solution. This hot mixture was then allowed to cool to about 250° C. to allow the growth of the CdSe nanocrystals. This readily reproducible preparation can be carried out under argon. The resulting as-prepared CdSe nanocrystals are highly luminescent with a photoluminescence (PL) quantum yield (QY) typically around 60%. Samples up to about 60% PL QY are also obtained in this fashion.

The use of non-coordinating solvent systems presents significant design advantages in the preparation of nanocrystals, because these solvents allow the reactivity of precursor monomers to be tuned by simply varying the ligand concentration in solution. This tunable reactivity provides the necessary balance between crystal nucleation and crystal growth, which is the key for controlling the size and size distribution of the resulting nanocrystals. In practice, such tunability has the great potential to promote the synthesis of various semiconductor nanocrystals to the level of that of the well-developed CdSe nanocrystals in coordinating solvents. This potential is explicitly demonstrated herein with successful synthetic schemes for producing high quality and monodisperse II–VI nanocrystals (for example CdS and CdTe) and III–V nanocrystals (for example InP and InAs). The narrow size distributions of as-prepared semiconductor nanocrystals obtained through the present reaction scheme may often be approached using existing synthetic schemes only after tedious size selective precipitations. In many cases, the size distribution of the size-selected samples prepared through existing coordinating-solvent methods is significantly worse than that of the as-prepared nanocrystals through the new methods described herein. Moreover, the quality of nanocrystals synthesized in non-coordinating solvents is at least comparable to those prepared by traditional organometallic synthesis in coordinating solvents, yet they are produced using far less dangerous and less toxic materials.

Non-coordinating solvents afford further practical advantages to the synthetic methods disclosed here. For example, at room temperature, ODE is liquid, rather than a solid as many coordinating solvents are, thereby contributing to the excellent processability of this synthetic system. The non-coordinating solvent based synthesis of this invention generally takes about 3–4 hours per sample preparation, which is significantly faster than the existing schemes using coordinating solvents (3–7 days per sample preparation for InP nanocrystals). (A. A. Guzelian, J. E. B. Katari, A. V. Kadavanich, U. Banin, K. Hamad, E. Juban, A. P. Alivisatos, R. H. Wolters, C. C. Arnold, J. R. Heath, *Journal of Physical Chemistry* 100 (1996) 7212; O. I. Micic, J. R. Sprague, C. J. Curtis, K. M. Jones, J. L. Machol, A. J. Nozik, H. Giessen, B. Fluegel, G. Mohs, N. Peyghambarian, *Journal of Physical Chemistry* 99 (1995) 7754; O. I. Micic, C. J. Curtis, K. M. Jones, J. R. Sprague, A. J. Nozik, *Journal of physical Chemistry* 98 (1994) 4966.) The cost of a typical non-coordinating solvent used in this invention, such as octadecene (ODE) is about 10–100 times less expensive than the most commonly used coordinating solvent, trioctylphosphine oxide (TOPO).

Accordingly, it is one aspect of the present invention to provide new synthetic methods for preparing II–VI, III–V, and other types of semiconductor "nanocrystals" that are both nanometer size and highly monodisperse.

It is a further aspect of this invention to provide a method for synthesizing highly monodisperse, semiconductor nanocrystals utilizing inexpensive, low or limited toxicity precursors materials.

Yet another aspect of the present invention is the development of a method of synthesizing monodisperse semiconductor nanocrystals using non-coordinating solvents.

Still another aspect of this invention is discovery of a method to control the polydispersity index (PDI) of semiconductor nanocrystals during their synthesis.

Still another aspect of this invention is the development of a method for the synthesis of shape-controlled nanocrystals, such as rods and branched nanocrystals, which are monodisperse on all three dimensions.

A further aspect of this invention is the development of a procedure for controlling the average size of the semiconductor nanocrystals prepared using non-coordinating solvents.

Another feature of this invention involves methods for improving the quality of nanocrystals synthesized in non-coordinating solvents, such that their quality is comparable or better than those prepared by traditional organometallic synthesis in coordinating solvents.

Another aspect of the present invention is the development of methods for synthesizing monodisperse CdS, CdSe, CdTe, ZnSe, InP, and InAs, without the need for size sorting.

Yet a further aspect of this invention is to develop synthetic methods for nanocrystals that may be carried out in reaction vessels open to the air, without the need for inert atmosphere.

An additional aspect of this invention is developing a synthetic scheme for monodisperse nanocrystals that using non-coordinating solvents that are liquid at room temperature, and processing and recycling procedures that contribute to the excellent processability of the system, and are amendable to recycling procedures.

Still another aspect of this invention is the development of synthetic procedures for preparing nanocrystals that allow more environmentally innocuous precursors, ligands, and solvents to be employed, and that are convenient, less expensive, safer, faster, and more environmentally "green" than methods currently used.

These and other features, aspects, objects and advantages of the present invention will become apparent after a review of the following detailed description of the disclosed embodiments and appended claims, in conjunction with the drawings described as follows.

DETAILED DESCRIPTION OF THE INVENTION

Figure 1:
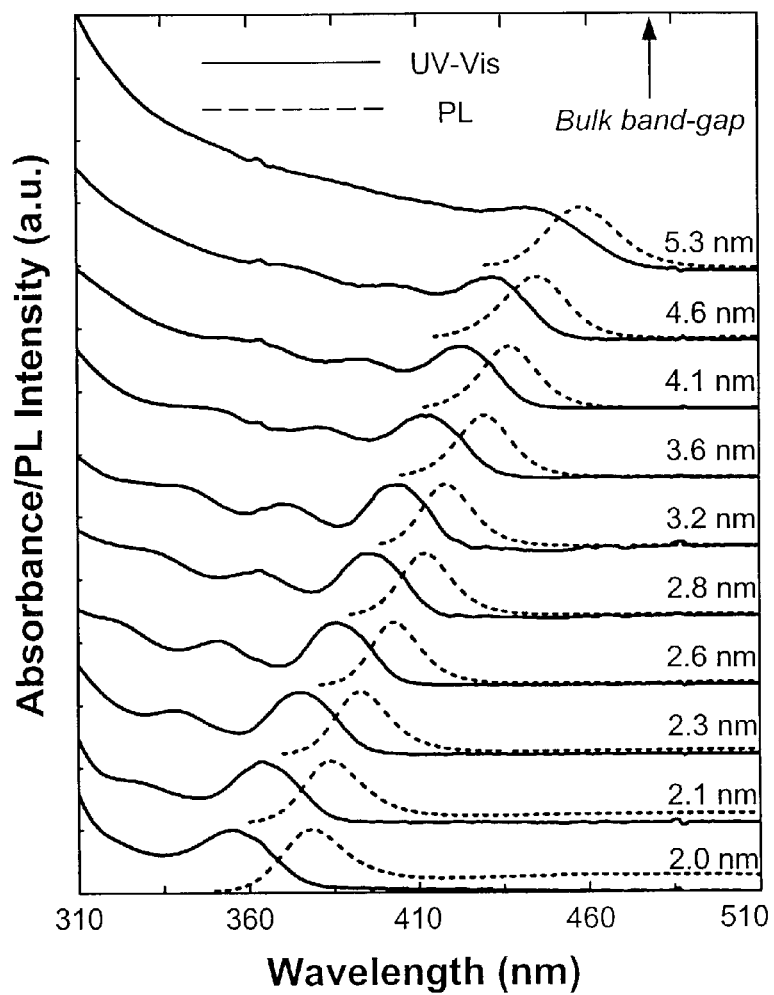
FIG. 1 exemplifies both the UV-Vis absorption spectra and photoluminescence (PL) spectra of the "as-prepared" CdS nanocrystals with different sizes, without any size separation or processing.

The present invention provides substantially monodisperse semiconductor nanocrystals, as well as new synthetic methods for selectively producing monodisperse nanocrystals. These methods provide tunable crystal sizes/shapes and size/shape distributions, are versatile and highly selective, and often provide higher quality crystals than present methods. It is established herein that coordinating solvents are not intrinsically required for the synthesis of high quality semiconductor nanocrystals, notwithstanding the conventional notion that coordinating solvents are necessary for preparing semiconductor nanocrystals.

The concept that less toxic, non-coordinating solvents could be effective at promoting nanocrystal synthesis was used as the basis for designing entire synthetic procedures which involve only the simplest and least toxic raw materials and do not generate or use any unnecessary toxic side-products or starting materials. Procedures of this type are sometimes called "least toxicity syntheses". This concept was further used to develop synthetic methods requiring only a fraction of the amount of organophosphine, organophosphine oxide, or other toxic compounds as existing synthetic schemes (as demonstrated herein for CdSe), referred to as "limited toxicity synthesis". For example, the least toxicity synthesis of CdS nanocrystals as described herein was performed in a simple reaction system, involving no organophosphorus or other expensive or highly toxic chemicals. Instead, oleic acid (OA) was used as a ligand and octadecene (ODE) acted as the solvent for both cadmium precursor (cadmium oleate, formed in situ by the reaction of CdO with oleic acid) and sulfur precursor (element sulfur). Apart from these four very commonly used compounds, no other chemical is required.

With reference to the Figures and the Examples presented herein, typical embodiments are disclosed using nanocrystals of the II–VI semiconductor and III–V semiconductor types. These examples are presented for illustration purposes and should not be construed as limiting the scope of the present invention.

Preparation and Properties of Monodisperse II–VI Semiconductor Nanocrystals

The formation of substantially monodisperse II–VI semiconductor nanocrystals using the new preparative methods of this invention is presented in detail for the synthesis of CdS nanocrystals, but also extends to other II–VI materials such as CdSe, CdTe, ZnSe, and the like.

Typically, the non-coordinating solvent used to prepare CdS nanocrystals was octadecene (ODE; $C_{18}H_{36}$), which is a liquid at room temperature and boils at about 320° C. Oleic acid (OA; $C_{18}H_{34}O_2$), a natural surfactant, was chosen as the ligand for stabilizing the resulting nanocrystals and the cation precursors. For the synthesis of CdS, the usual precursors were CdO and elemental sulfur, both of which are natural minerals. An ODE solution of elemental sulfur can be used as the sulfur precursor solution for the formation of CdS nanocrystals. It is believed that this system is even less toxic than the synthesis of CdS nanocrystals in aqueous solution, which uses $H_2S$, $Na_2S$ or similar toxic and noxious chemicals, and provides nanocrystals of substantially lower quality than those provided herein. (T. Vossmeyer, L. Katsikas, M. Giersig, I. G. Popovic, K. Diesner, A. Chemseddine, A. Eychmuller, H. Weller, *Journal of Physical Chemistry* 98 (1994) 7665.)

In a typical synthesis, CdO was dissolved in ODE through its reaction with oleic acid (OA) at elevated temperatures. The CdO, OA, ODE mixture was maintained at around 300° C., while a sulfur solution (elemental sulfur in ODE) was swiftly injected into the hot solution. This hot mixture was then allowed to cool to about 250° C. to allow the growth of the CdS nanocrystals. This preparation can be performed under an argon flow without degassing the reaction system, and can even be performed in air without sacrificing the quality of the nanocrystals. Reaction progress was monitored by UV-Vis absorption spectroscopy and photoluminescence (PL) spectra by sampling aliquots from the reaction flask.

Useful non-coordinating solvents for preparing high quality semiconductor nanocrystals are generally selected using the following guidelines. First, the solvent should possess a relatively high boiling point (around 300° C. or higher) for growing highly crystalline nanocrystals and a relatively low melting point (approximately 20° C. or lower) for a convenient, room temperature workup after synthesis. The high boiling point preference is based on the fact that the high quality semiconductor nanocrystals are typically synthesized at high temperatures. However, low temperature semiconductor nanocrystal synthetic methods have also been developed. For example, we have recently developed a process by which CdSe nanocrystals can be grown at about 100° C., indicating that water may be able to act as a solvent for the growth of high quality semiconductor nanocrystals. Typically, useful non-coordinating solvents will have a melting point less than about 25° C. and a boiling point greater than about 250° C. Second, reactants and products alike should be soluble and stable in the selected solvent. Third, the solvent should be as universal as possible for its ability to dissolve common starting materials and therefore for synthesizing high quality inorganic nanocrystals. Finally, the solvent should be safe, relatively inexpensive, and easy to dispose of or recycle. Based on these standards, the traditional coordinating solvent, TOPO, is significantly worse than the coordinating solvents, since it has a high melting point (about 60° C.), and is quite expensive and toxic.

Using the four standards set forth above, it was determined that Technical grade ODE (Aldrich Chemical Company, Milwaukee, Wis.) is a good solvent choice. Although it is a technical grade reagent, the impurities (10%) are all alkenes with very similar physical and chemical properties to those of ODE. Therefore, it was expected that technical grade ODE would be an inexpensive choice without sacrificing the desirable characteristics. The boiling point of Tech-ODE is about 310–340° C. at 1 atm, and its melting point is between 15–17° C. Apparently, the double bond of ODE increases its boiling point and decreases its melting point in comparison to octadecane. In addition to the above advantages, element sulfur has a significant solubility in Tech ODE, which may be a result of the slight polarity of the double bond. We also note that in some preparations, certain ethers can constitute reasonable non-coordinating solvents.

FIG. 1 presents UV-Vis absorption spectra and photoluminescence (PL) spectra of high quality CdS nanocrystals formed in ODE, where the average particle size for each spectrum is further provided in the plot. Based on the co-inventors' knowledge in this field, the UV-Vis absorption and PL spectra shown in FIG. 1 are the sharpest ones for CdS nanocrystals synthesized in any solvent, indicating a very narrow size distribution of the nanocrystals formed in ODE. (C. B. Murray, D. J. Norris, M. G. Bawendi, *Journal of the American Chemical Society* 115 (1993) 8706; Z. A. Peng, X. Peng, *J. Am. Chem. Soc.* 123 (2001) 183; T. Vossmeyer, L. Katsikas, M. Giersig, I. G. Popovic, K. Diesner, A. Chemseddine, A. Eychmuller, H. Weller, *Journal of Physical Chemistry* 98 (1994) 7665.) FIG. 1 also reveals the high monodispersity that can be achieved in this invention by examining the photoluminescence emission line of the nanocrystals, which can have a full width at half maximum (FWHM) as narrow as 23–24 nm, with typical FWHM values of around 18–25 nm. These as-prepared nanocrystals are further characterized by the photoluminescence quantum yield (PL QY) of up to about 60%.

The PL of the CdS nanocrystals is dominated by their band edge emission, except for those spectra for the nanocrystals smaller than about 2 nm in diameter (data not shown), which is usually not the case for CdS nanocrystals. The achievable size range shown in FIG. 1 is also plausible when compared to the existing synthetic schemes. (C. B. Murray, D. J. Norris, M. G. Bawendi, *Journal of the American Chemical Society* 115 (1993) 8706; Z. A. Peng, X. Peng, *J. Am. Chem. Soc.* 123 (2001) 183; T. Vossmeyer, L. Katsikas, M. Giersig, I. G. Popovic, K. Diesner, A. Chemseddine, A. Eychmuller, H. Weller, *Journal of Physical Chemistry* 98 (1994) 7665.) The non-coordinating solvent approach presented here can reproducibly and controllably generate CdS nanocrystals in almost the entire quantum confined size regime (about 1–6 nm), with the first exciton absorption peak from 305 nm to about 440 nm. Example 7 and Table 1 demonstrate how the time of reaction is correlated with CdS nanocrystal size in a single reaction.

Figure 2:
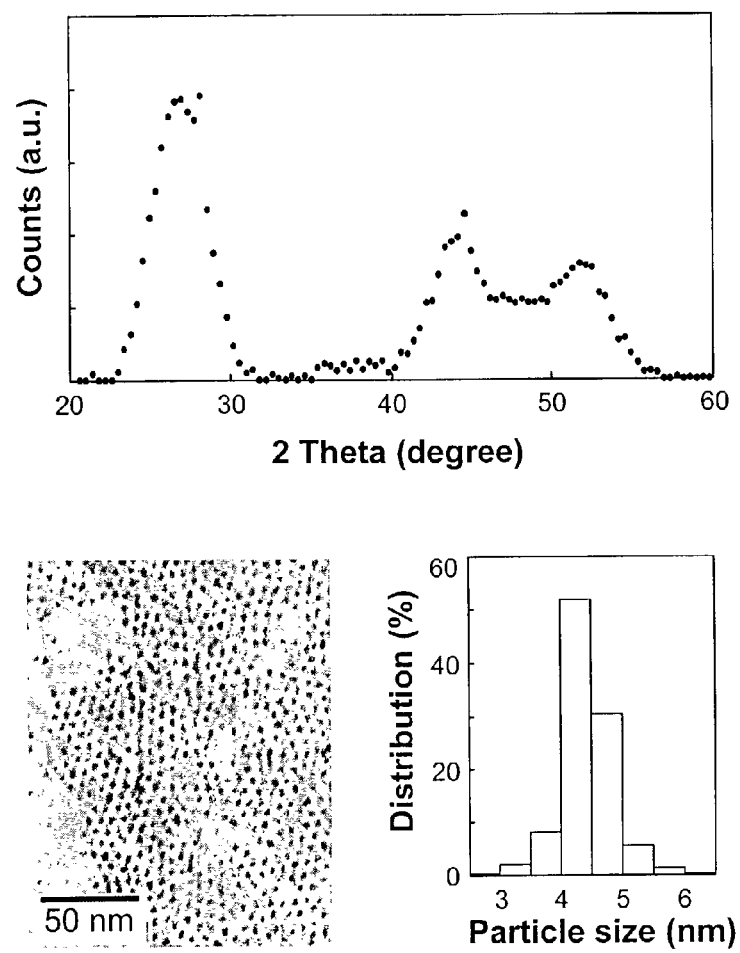
FIG. 2 is a representation of the X-ray diffraction pattern (top), TEM image (bottom, left), and the related size distribution diagram of the CdS nanocrystals (bottom, right).

Transmission electron microscope (TEM) measurements (FIG. 2) confirmed that the size distribution of the as-prepared CdS nanocrystals was nearly monodisperse in the entire size range mentioned above, with a relative standard deviation of around 5–15% without any size sorting. The diffraction pattern (FIG. 2) seems to resemble that of wurtzite nanocrystals with one or more zinc-blende stacking faults along the c axis. (C. B. Murray, D. J. Norris, M. G. Bawendi, *Journal of the American Chemical Society* 115 (1993) 8706.)

Figure 3:
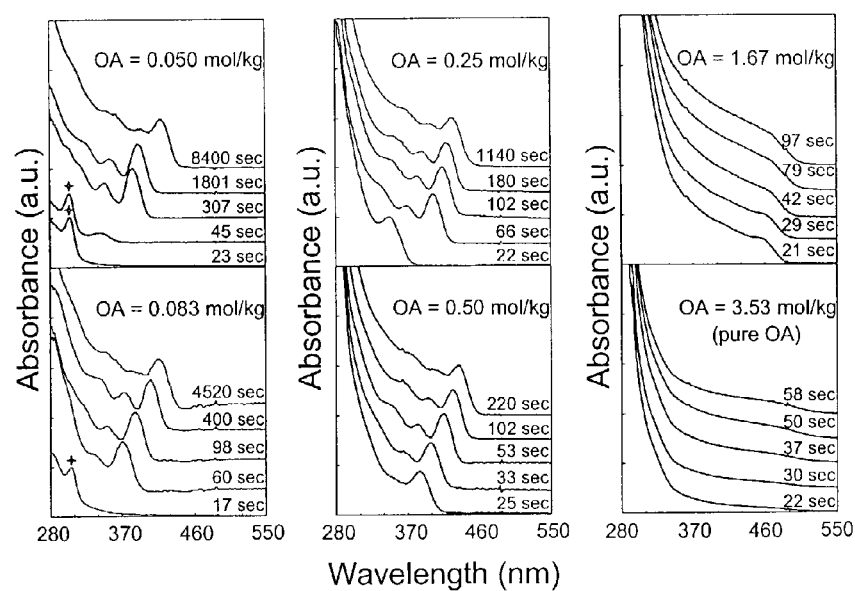
FIG. 3 demonstrates the temporal evolution of the absorption spectrum of the CdS nanocrystals grown in ODE with different oleic acid concentrations. The absorption peaks dedicated to a magic sized nanocluster are marked with a star.

The data shown in FIG. 3 indicate that a temporal window of "focusing of size distribution" was observed shortly after the reaction started by the injection of the sulfur solution for the reactions with relatively low ligand concentrations, as indicated by the sharpening of the absorption features over time (FIG. 3). (X. Peng, J. Wickham, A. P. Alivisatos, *Journal of the American Chemical Society* 120 (1998) 5343.) The instantaneous appearance of a focusing window after the initiation of the reaction indicates that the nucleation occurred in a very short period of time, after which substantially all of the nuclei formed grew almost simultaneously due to the relatively high concentrations of the remaining monomers after the nucleation process. Focusing also indicates that the smaller nanocrystals grow faster than the large nanocrystals such that the size distribution narrows. It is likely that growth of CdS nanocrystals in this system is diffusion controlled. It is well-established that, with an instantaneous nucleation, a diffusion controlled growth should possess a very efficient focusing behavior as the nanocrystals grow, which is exactly the case shown in FIG. 3. If the reaction was allowed to proceed for a long time, defocusing of size distribution or Ostwald ripening would occur. (X. Peng, J. Wickham, A. P. Alivisatos, *Journal of the American Chemical Society* 120 (1998) 5343.) The reaction data shown in FIGS. 1–3 can be used to guide the synthesis of CdS nanocrystals to provide samples with a narrow size distribution, between about 1 nm and about 6 nm. This size range can be further tuned by changing the injection temperature, the growth temperature, the concentration of oleic acid and monomers, the molar ratio of the two precursors, and the like, so that the balance between nanocrystal nucleation and growth is maintained. Adjusting some of these parameters results in complex behavior in the evolution of the resulting nanocrystal size and size distribution. For example, increasing the injection temperature does not always result in a simple increase in the reaction rate, but rather often results in a slower reaction between precursors. This complex behavior usually contrasts to the more simple behavior seen upon increasing the nanocrystal growth temperature, which typically results in faster crystallization, faster approach to the focusing window, and faster approach to the desired nanocrystal size. However, one of ordinary skill can readily and empirically correlate the change in reaction parameters to resulting nanocrystal size and size distribution in the same way that FIGS. 1–3 demonstrates for CdS. (W. W. Yu, X. Peng, *Angew. Chem. Int. Ed.* 41 (2002), 2368; X. Peng, J. Wickham, A. P. Alivisatos, *J. Am. Chem. Soc.* 120 (1998) 5343.) Among all these parameters, adjusting the concentration of the ligands for cadmium monomers and CdS nanocrystals, in this case oleic acid, is a parameter which does not exist in a synthesis performed in coordinating solvents. Experimental results disclosed herein reveal that by adjusting the concentration of oleic acid, the reaction kinetics could be totally altered even if all other parameters were fixed (FIG. 3).

The influence of OA ligand concentration on the growth kinetics of CdS nanocrystals, and other types of semiconductor nanocrystals, is dramatic. FIG. 3 illustrates the temporal evolution of the absorption spectrum of the CdS nanocrystals grown in ODE, using different oleic acid (OA) concentrations. Thus, all the data in FIG. 3 were obtained under identical reaction conditions, except for the concentration of OA in the reaction mixture. With pure oleic acid as the coordinating solvent (OA concentration=3.53 mol/kg), only a small amount of bulk sized CdS particles were observed. As the concentration of OA in ODE solvent decreased, the growth rate of the nanocrystals slowed systematically, and the size distribution of the resulting nanocrystals became significantly narrower at the focusing point of the size distribution, indicated by the sharpness of the first (shortest time) absorption peak of the sharpest spectrum in each series. (X. Peng, J. Wickham, A. P. Alivisatos, *Journal of the American Chemical Society* 120 (1998) 5343.) Thus, low concentrations of OA provided the most monodisperse CdS nanocrystals. These experiments demonstrate the ability that this synthetic procedure imparts to lower the polydispersity index (PDI) by lowering ligand concentration.

Figure 4:
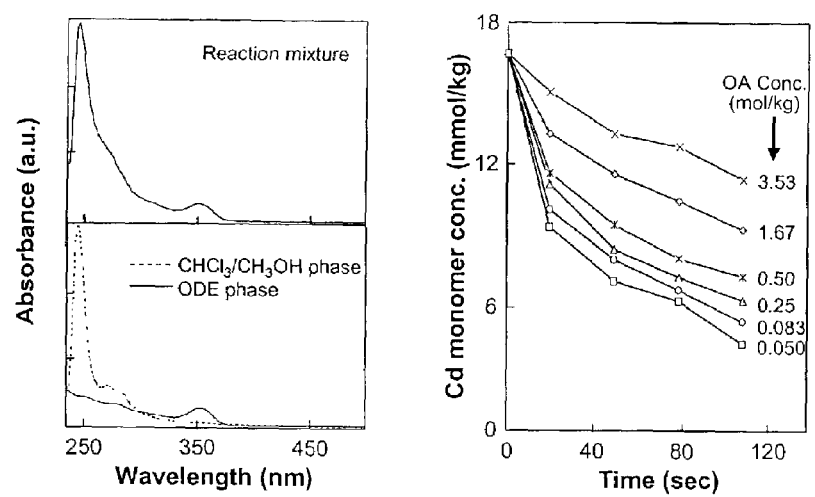
FIG. 4 illustrates the following. Left: Spectroscopic demonstration of the separation of CdS nanocrystals from oleic acid and unreacted cadmium oleate. Right: Temporal evolution of the monomer concentrations in ODE with different oleic acid concentrations.

The influence of OA ligand concentration in a non-coordinating solvent is the result of the tuned reactivity of the cation monomers in the non-coordinating solvent, where the term "cation monomer" refers to all cadmium species (or other metal species, as applicable) in the solution not in the form of nanocrystals. In the following experiment, a reaction mixture for the synthesis of CdS in ODE, after a given reaction time (indicated in FIG. 3) was sampled and separated to two fractions by extraction with a 1:1 (v:v) mixture of $CHCl_3$ and $CH_3OH$. The CdS nanocrystals appear to be soluble only in the ODE phase, whereas oleic acid and cadmium oleate are both extracted into the $CHCl_3/CH_3OH$ phase. Such separation was confirmed by UV-Vis and FTIR measurements (FIG. 4 Left). After this separation, the concentration of unconverted cadmium oleate in the reaction solution was determined by atomic absorption spectroscopy (FIG. 4, Right). As seen in FIG. 4, the cadmium monomer concentration in the solution dropped very quickly within the first 20 seconds, and the rate of this depletion increased as the oleic acid concentration decreased (FIG. 4, Right). From the spectra shown in FIG. 3, one can find that the average size of the nanocrystals at about 20 seconds after the injection decreased systematically as the initial oleic acid concentration decreased. Similar results were obtained for the formation of other types of semiconductor nanocrystals. Combining these facts, one can conclude that the number of the nanocrystals (nuclei) formed in the initial nucleation stage increased significantly as the initial oleic acid concentration decreased. This conclusion indicates that the reactivity of the monomers in the solution increases significantly when the ligand concentration in solution decreases.

In contrast, the depletion rate of the monomers did not change much with a different initial oleic acid concentration after the initiation stage of the reactions, although the remaining monomer concentration was higher for the reactions with a higher oleic acid concentration. While not intending to be bound by the following statement, it is likely this effect is caused by two conflicting factors. In comparison to a reaction with a lower ligand concentration, the reactivity of the monomers of a give reaction was lower, but the remaining concentration of the monomers was higher.

According to the current understanding, the influence of the ligand concentration in controlling the size distribution of growing colloidal nanocrystals is achieved by a balance between nucleation and growth. A successful synthetic scheme should start with a fast and short nucleation period, which is followed by a growth stage without either prolonged nucleation or ripening, which is referred as "focusing of size distribution". (X. Peng, J. Wickham, A. P. Alivisatos, *Journal of the American Chemical Society* 120 (1998) 5343.) If too many nuclei were formed in the initial nucleation period, the remaining monomers would not be sufficient to promote the focusing of size distribution for a sufficient time, and this would result in an undesired Ostwald ripening or "defocusing" of size distribution. If too few nuclei formed, the growth reaction would be too fast to be controlled to reach desired size and size distribution. To achieve this balance between nucleation and growth, a nearly continuous tunable reactivity of the monomers is desirable. As discussed above, such tunability can be readily achieved by simply altering the ligand concentration in a non-coordinating solvents. This tunability may indicate that the cadmium monomers in the solution at elevated temperatures are not simply cadmium oleate. The number of "nearby" ligands for each cadmium ion may strongly depend on the concentration of the ligands in the bulk solution. Consequently, the reactivity of those cadmium complexes at elevated temperatures varies with the ligand concentration in solution.

Similar results were obtained for the synthesis of other types of II–VI semiconductors, such as ZnSe, CdSe, and CdTe nanocrystals, in ODE using fatty acids or other ligands. Elemental sulfur, selenium, or tellurium dissolved in ODE were employed as the anionic precursors for the synthesis of II–VI semiconductor nanocrystals. (W. W. Yu, X. Peng, *Angew. Chem. Int. Ed.* 41 (2002), 2368; Z. A. Peng, X. Peng, *J. Am. Chem. Soc.* 123 (2001) 183; C. B. Murray, D. J. Norris, M. G. Bawendi, *Journal of the American Chemical Society* 115 (1993) 8706.) In the case of selenium and tellurium elements, a small amount of organophosphine is typically used to assist the dissolution of the elements in ODE.

Nanocrystals of ZnSe, regardless of their size, cannot be formed in pure OA, pure trioctylphosphine oxide (TOPO), or a mixture of a fatty acid and TOPO as the coordinating solvent. Attempts to prepare ZnSe using traditional organometallic approaches (for example with $Zn(CH_3)_2$ as a precursor), also failed in these pure coordinating solvents. However, ZnSe nanocrystals with acceptable monodispersities were formed in dilute OA solutions in ODE using $Zn(Ac)_2$, Se-TBP, OA and ODE reaction mixtures. Similarly, it is also not practical to synthesize CdSe nanocrystals with relatively small sizes (<4 nm) in pure fatty acids, nor in fatty acid-TOPO mixtures. (Z. A. Peng, X. Peng, *J. Am. Chem. Soc.* 123 (2001) 183.) However, a suitable amount of OA ligand in ODE as the non-coordinating solvent generates a relatively monodisperse sample of CdSe nanocrystals, from CdO and Se, the size of which can be selected from approximately 1.5 nm to about 20 nm in a controllable fashion. With long chain amines added as the co-ligands in the reaction mixture, the reaction further yields CdSe nanocrystals with very high PL QY.

Figure 5:
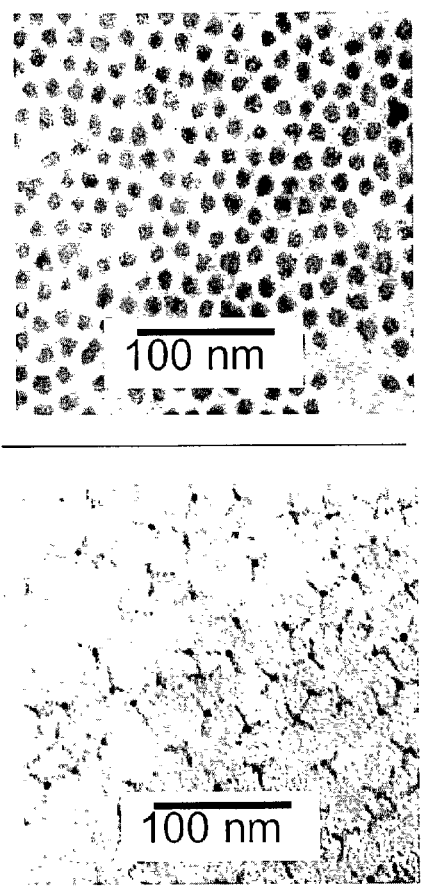
FIG. 5 illustrates the TEM images of the as-prepared CdTe nanocrystals. Top: Dot-shaped CdTe nanocrystals. Bottom: Tetrapole-shaped CdTe nanocrystals.

Non-coordinating solvents also generated CdTe nanocrystals with superior control over their size, shape, size/shape distribution in a large size range, between about 1 to 20 nm. FIG. 5 illustrates the TEM images of as-prepared CdTe nanocrystals, which exhibit different shapes as a function of reaction conditions and reagents used. For example, the dots produced in FIG. 5, top, are prepared from Te in PBu$_3$ or P(hexyl)$_3$ with OA as the ligand, while the tetrepoles (tetrahedral shaped) nanocrystals in FIG. 5, bottom, are prepared from Te in P(octyl)$_3$ with OA as the ligand. Further, shape adjustments also may result from concentration adjustments in the ligand. The PL QY of the CdTe nanocrystals produced by this method is typically around 50%.

A range of ligands could be used in the preparation of II–VI semiconductor nanocrystals. For example, numerous fatty acids, amines, phosphonic acids, phosphines, phosphine oxides, various surfactants and the like, were found to be good ligands for the synthesis of CdSe, CdS, and CdTe nanocrystals in non-coordinating solvents. (L. Qu, Z. A. Peng, X. Peng, *Nano Lett.* 1 (2001) 333.)

These results indicate how the temporal course of the nucleation and growth of semiconductor nanocrystals can be continuously tuned by simply changing the concentration of the ligands in a non-coordinating solvent. Such flexibility is impossible for a synthesis preformed in coordinating solvents. Appropriate reactivity of the monomers, manipulated by varying the ligand concentration in non-coordinating solvents, led to a balance between the two conflicting requirements of a successful synthetic scheme: a fast but short nucleation stage and a slow but long growth stage without Ostwald ripening. (X. Peng, J. Wickham, A. P. Alivisatos, *Journal of the American Chemical Society* 120 (1998) 5343.) Solvents other than ODE could also provide suitable reaction media for preparing semiconductor nanocrystals.

Preparation and Properties of Monodisperse III–V Semiconductor Nanocrystals

The synthesis of nanocrystals of III–V semiconductors such as InP is significantly more condition-sensitive than that of II–VI semiconductor nanocrystals, in that typical procedures, ligands, and precursors with analogous compositions employed in the preparation of high quality II–VI semiconductor nanocrystals usually did not provide for the growth of high quality III–V nanocrystals. Within the experimental conditions explored for InP crystallization, certain fatty acids with well-defined chain lengths, a non-coordinating solvent, a well-controlled indium to ligand ratio, and a thorough degassing process are all significant factors for synthesizing high quality InP nanocrystals, without requiring any size sorting. These observations have been generally applicable for developing synthetic methods for other III–V semiconductor nanocrystals such as InAs.

In a typical synthesis, In(Ac)$_3$ (where Ac=acetate, O$_2$CCH$_3$) was mixed with the desired ligand in non-coordinating ODE solvent. This mixture was heated and degassed under vacuum, followed by purging with argon to afford an inert atmosphere for the reaction and crystallization. A sample of P(TMS)$_3$ (where TMS=Si(CH$_3$)$_3$) dissolved in ODE under an inert atmosphere was injected into the hot In/ligand/ODE solution, and the temperature was subsequently lowered to grow the InP nanocrystals. Both single and multiple injections of P(TMS)$_3$ were employed. For multiple injections, successful secondary injections were performed dropwise by alternating injections of indium and phosphorus solutions in about half the molar concentration of the original solutions. While various ratios of indium to phosphorus reagents can be used, the best results for both single and multiple injection reactions were achieved by maintaining about a 2:1 indium to phosphorus molar ratio. The resulting InP nanocrystals could be dissolved in typical non-polar solvents. No size sorting was performed on any of the samples used in the measurements.

A typical synthesis of II–VI semiconductor nanocrystals in non-coordinating solvents such as ODE, does not require degassing the entire reaction system, and performing the reaction under a flow of inert gas such as argon is not essential. If fact, the entire process can even be performed in air without sacrificing the quality of the CdS nanocrystals. (W. W. Yu, X. Peng, *Angew. Chem. Int. Ed.* 41 (2002), 2368; L. Qu, X. Peng, *Journal of the American Chemical Society* 124 (2002) 2049; Z. A. Peng, X. Peng, *Journal of the American Chemical Society* 124 (2002) 3343; Z. A. Peng, X. Peng, *J. Am. Chem. Soc.* 123 (2001) 183.) In contrast, a thorough degassing step was found important for the synthesis of InP nanocrystals, indicating that Inp nanocrystals are sensitive to the atmosphere. While elemental sulfur, selenium, or tellurium dissolved in ODE were used as the precursors for the synthesis of II–VI semiconductor nanocrystals, (W. W. Yu, X. Peng, *Angew. Chem. Int. Ed.* 41 (2002), 2368; Z. A. Peng, X. Peng, *J. Am. Chem. Soc.* 123 (2001) 183; C. B. Murray, D. J. Norris, M. G. Bawendi, *Journal of the American Chemical Society* 115 (1993) 8706) an analogous method was not useful in the III–V nanocrystal synthesis. For example, elemental phosphorus was not reactive enough to initiate the formation of InP nanocrystals in ODE (or in a variety of coordinating solvents). In$_2$O$_3$ (unlike CdO) was also not found to be feasible for the synthesis of InP nanocrystals because it is insoluble in ODE in the presence of the desired ligands.

Despite the general belief that coordinating solvents are necessary for preparing semiconductor nanocrystals, non-coordinating solvents were used in preparing III–V nanocrystals. Octadecene (ODE) was employed as the non-coordinating solvent in the synthesis of InP and InAs, for the reasons disclosed above. A number of coordinating compounds such as fatty acids, amines, phosphines, phosphine oxides, phosphonic acids, and the like were tested as pure coordinating solvents, and provided lower quality nanocrystals than those prepared in a non-coordinating solvent. Although many of these ligands are useful for synthesizing the II–VI nanocrytals such as CdSe, CdS, and CdTe in coordinating or non-coordinating solvents, most did not prove optimal for growing high quality InP nanocrystals. For relatively weakly-coordinating ligands such as amines, phosphine oxides, and certain fatty acids, continuous nucleation was common, thereby increasing the sample polydispersity. With stronger ligands, such as phosphonic acids, no reaction was observed under typical reaction conditions. The use of coordinating solvents usually generated nanocrystals without a distinguishable absorption peak in the UV-Vis absorption spectrum, implying a broad size distribution.

Figure 6:
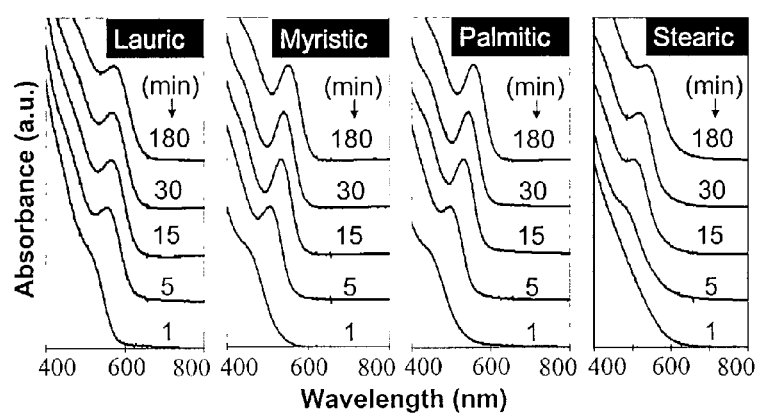
FIG. 6 illustrates the temporal evolution of UV-Vis spectra of InP nanocrystals grown with fatty acids as the ligands, where the indium:acid ratio=1:3 for all reactions.

Among all ligands tested, fatty acids with certain chain lengths were found to be the best ligands using ODE as the non-coordinating solvent. FIG. 6 illustrates the temporal evolution of the UV-Vis absorption spectra of InP nanocrystals formed in ODE using fatty acids with different chain lengths as the ligands. Decanoic acid (DA; $C_{10}H_{20}O_2$), Lauric acid (LA; $C_{12}H_{24}O_2$), myristic acid (MA; $C_{14}H_{28}O_2$), palmitic acid (PA; $C_{16}H_{32}O_2$), stearic acid (SA; $C_{18}H_{36}O_2$), and oleic acid (DA; $C_{18}H_{34}O_2$) were tested. The data presented in FIG. 6 indicate that palmitic acid (PA) and myristic acid (MA) provide the most monodisperse samples of nanocrystals. It has been found that typically, the longer the hydrocarbon chain of the fatty acid, the slower the resulting nanocrystal nucleation and growth. While not intending to be bound by the following statement, it is believed that the fatty acids with intermediate chain lengths such as PA and MA are the best ligands for providing the desired balance between nucleation and growth rate for the growth of relatively monodisperse InP nanocrystals.

Figure 7:
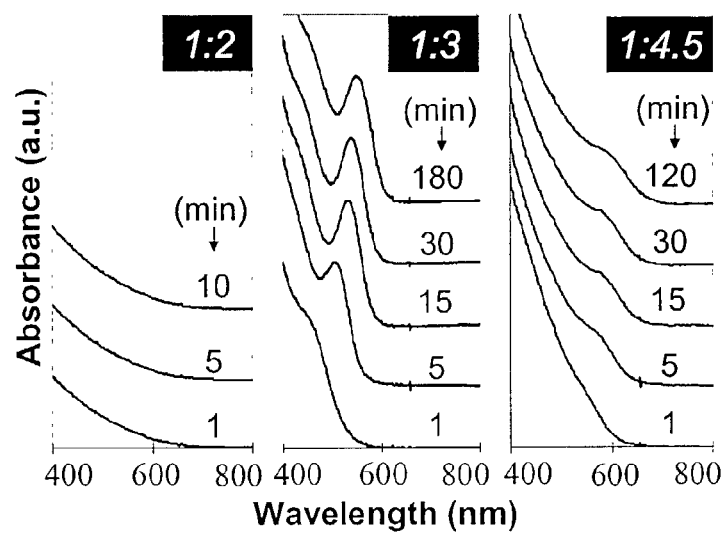
FIG. 7 demonstrates the temporal evolution of UV-Vis spectra of InP nanocrystals grown at 270° C. with different In:MA ratios in ODE, where MA is myristic acid.

Optimizing the present synthesis of highly monodisperse nanocrystals in solution also used the principle of "focusing of size distribution", which dictates that a quick and short nucleation process, followed by a relatively slow and long growth process, and which optimizes the sample monodispersity. Thus, as disclosed above for II–VI semiconductor nanocrystal synthesis, the concentration of the ligands in a non-coordinating solvent tunes the reactivity of the metal (or cation) precursors to reach the desired balance between nucleation and growth for the formation of high quality nanocrystals. For III–V nanocrystals such as InP, the effect of ligand concentration is even more dramatic than for the II–VI nanocrystals described above. FIG. 7 shows that when the molar ratio of In:MA in the solution was about 1:3, the reaction generated InP nanocrystals with a good size distribution, as indicated by the well-distinguished absorption features. When the In:MA molar ratio was varied to either about 1:2 or about 1:4.5, the reaction either proceeded out of control, or generated nanocrystals without any distinguishable absorption peak, implying a broad size distribution. These results indicate that the available window of ligand concentrations for forming high quality InP nanocrystals, and possibly for other types of III–V nanocrystals, is relatively narrow.

Figure 8:
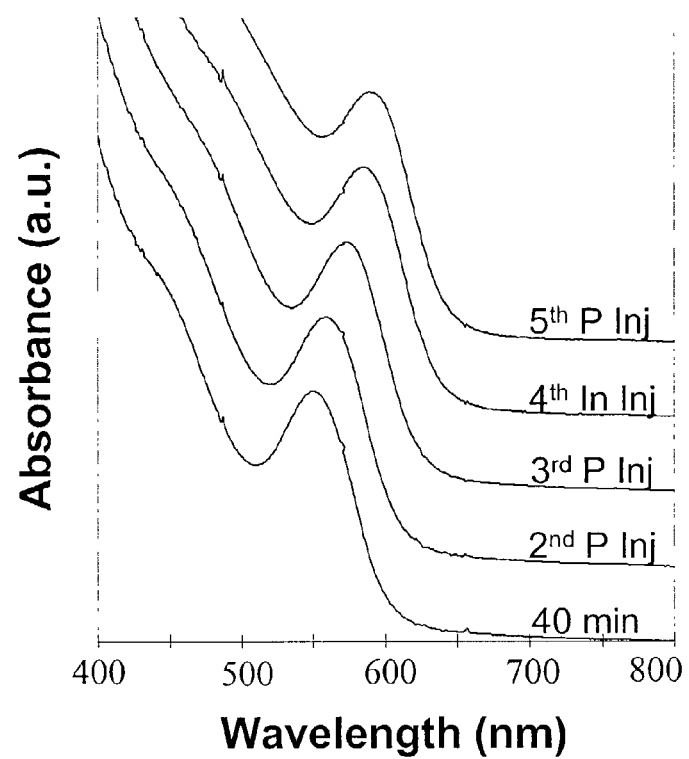
FIG. 8 is a representation of the UV-Vis spectra of InP nanocrystals grown by multiple injections. A secondary injection was performed after the nanocrystals grew for 5–10 minutes without changing the absorption spectrum.

As shown in FIG. 8 for InP, certain secondary injection methods were found feasible for varying the size of the resulting III–V nanocrystals. Reaction temperatures for secondary injections are typically lower then the initial reaction temperature, for example, about 250° C. or less. In the case for InP crystallizations using secondary injection methods, the indium precursor and phosphorus precursor are added separately and in an alternating manner. When secondary injections were carried out at about 270° C. (representing the growth temperature after the primary injection), or using indium and phosphorus precursors in a single solution, resulted in a broad size distribution, presumably due to the continuous nucleation caused by the secondary injections.

Figure 9:
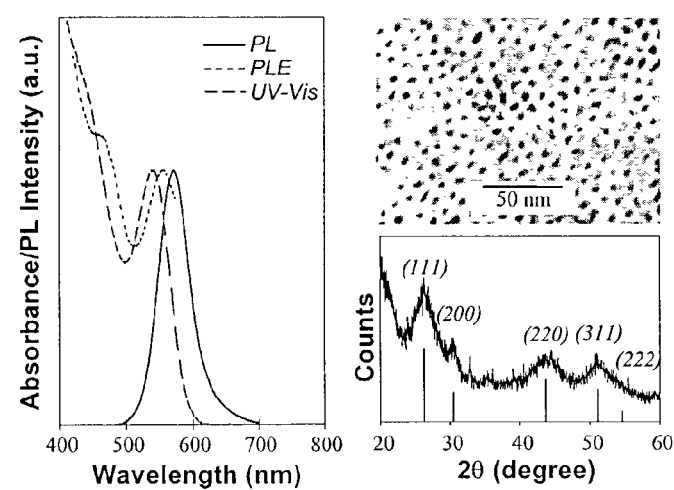
FIG. 9 represents the following. Left: PL, photoluminescence excitation (PLE), and UV-Vis spectra of InP nanocrystals. Right-Top: Transmission Electron Microscope (TEM) image of InP nanocrystals. Right-Bottom: XRD pattern of InP nanocrystals.

The photoluminescence (PL) spectrum of the InP nanocrystals constitutes solely a band-edge emission (FIG. 9, left). Transmission electron microscope (TEM) images of InP nanocrystals revealed that the crystals are generally in a dot-shape mixed with some slightly elongated ones (FIG. 9, top right). The size of the nanocrystals shown in FIG. 9 is 3.1 nm±4.7% by measuring 350 nanocrystals. The powder X-ray diffraction (XRD) pattern of the InP nanocrystals matches that of the zinc-blende structure of bulk InP crystals, including the (200) diffraction peak which is often difficult to resolve (FIG. 9, bottom-right). (A. A. Guzelian, J. E. B. Katari, A. V. Kadavanich, U. Banin, K. Hamad, E. Juban, A. P. Alivisatos, R. H. Wolters, C. C. Arnold, J. R. Heath, *Journal of Physical Chemistry* 100 (1996) 7212; O. I. Micic, J. R. Sprague, C. J. Curtis, K. M. Jones, J. L. Machol, A. J. Nozik, H. Giessen, B. Fluegel, G. Mohs, N. Peyghambarian, *Journal of Physical Chemistry* 99 (1995) 7754; O. I. Micic, C. J. Curtis, K. M. Jones, J. R. Sprague, A. J. Nozik, *Journal of Physical Chemistry* 98 (1994) 4966.)

The synthesis of other III–V semiconductor nanocrystals was performed in a manner similar to that described above for InP. For example, InAs nanocrystals were prepared in a similar manner as InP, using $In(Ac)_3$ and $As(TMS)_3$ as cation and anion precursors, respectively, in the presence of fatty acids as the ligand, all in the non-coordinating solvent ODE. However, in contrast to the InP synthesis, all fatty acids tested with hydrocarbon chain length between 10 and 22 carbon atoms were found to be suitable ligands for the formation of InAs nanocrystals. The temporal evolution of the very sharp absorption spectra of the resulting InAs nanocrystals, shown in FIG. 10, indicate that the size distribution of the sample produced in this fashion is superiorly narrow. Other III–V semiconductor nanocrystals could be prepared in the above mentioned ways and their variations.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to one of ordinary skill in the art without departing from the spirit of the present invention or the scope of the appended claims.

EXAMPLE 1

Preparation of Monodisperse CdS Nanocrystals in a Non-Coordinating Solvent

In a typical synthesis, a mixture of 0.10 mmol (0.0128 g) of CdO, 1.5 mmol (0.4237 g) of oleic acid, and 3.5635 g of technical grade octadecene (ODE, Aldrich Chemical Co., Milwaukee, Wis.), was prepared and heated. This mixture became optically clear at around 200° C., and was further heated up to about 300° C. and maintained at this temperature for the injection of the sulfur solution. A sulfur solution was prepared by dissolving 0.05 mmol (0.0016 g) of elemental sulfur in 2 grams of technical grade ODE. The preparation of the sulfur solution often required heating up the sulfur/Tech ODE mixture to about 100° C., allowing the sulfur powder to completely dissolve, and then cooling the solution to room temperature. The resulting, optically clear solution was stable at room temperature and ready for the injection. This sulfur solution was then swiftly injected into the hot, cadmium-containing solution with stirring, after which the reaction mixture was allowed to cool to about 250° C. for about 0.5 h, to allow the growth of the CdS nanocrystals. The synthesis can be done either under argon or open to air.

In order to monitor the progress of the synthesis and crystallization, aliquots of the reaction mixture prepared in this manner were taken at different time intervals, and UV-Vis and PL (photoluminescence) spectra were recorded for each aliquot. XRD (powder X-ray diffraction) and TEM (transmission electron microscopy) measurements were also performed to characterize the crystallinity, size, and size distribution of the resulting nanocrystals. The size distribution diagrams were obtained by measuring about 500 individual CdS nanocrystalline particles using enlarged photographs. All the measurements were performed on the original aliquots without any size sorting of the nanocrystals. The separation of the unreacted cadmium precursor from the resulting nanocrystals was accomplished by the repeated extractions of the reaction aliquots in ODE with an equal volume of a 1:1 mixture solvent of $CHCl_3$ and $CH_3OH$. The extraction process was also monitored by a UV-Vis absorption spectrophotometer, to determine when the resulting ODE nanocrystal solution was free from unreacted precursor materials.

For the experiments to vary the ligand-to-metal ratio, or to determine the effect of ligand-to-metal ratio, the amount of oleic acid was typically varied from about 0.30 mmol to about 21.2 mmol, as compared to 0.10 mmol (0.0128 g) of CdO, with the same amounts of sulfur and solvent as described above.

EXAMPLE 2

Preparation of Monodisperse CdSe Nanocrystals in a Non-Coordinating Solvent

The synthesis of CdSe nanocrystals was carried in a similar fashion as described in Example 1 using CdO as the cation precursor, in which the selenium source for injections was an ODE solution of selenium-tributylphosphine (1:1.1 ratio). The Se-TBP or other selenium organophosphine compounds was prepared simply by dissolving Se in a desired amount of liquid organophosphine. The injection solution was further prepared by diluting the Se-phosphine solution with an adequate amount of ODE.

For the synthesis of CdSe nanocrystals with high PL QY, long chain amines, such as hexadecylamine (HDA) and octadecylamine (ODA), were used as the co-ligands.

EXAMPLE 3

Preparation of Monodisperse CdTe Nanocrystals in a Non-Coordinating Solvent

The synthesis of CdTe nanocrystals was carried in a similar fashion as described in Example 1 using CdO as the cation precursor, in which the tellurium source for injections was an ODE solution of tellurium-tributylphosphine. The Te-TBP or other tellurium organophosphine compounds was prepared simply by dissolving Te in a desired amount of liquid organophosphine. The injection solution was further prepared by diluting the Te-phosphine solution with an adequate amount of ODE. The as-prepared CdTe nanocrystals possess very high PL QY, typically around 50%, without any further treatment. To maintain the bright emission of the CdTe nanocrystals, the as-prepared nanocrystals should be stored under air-free conditions, which is different from the bright CdSe nanocrystals.

EXAMPLE 4

Preparation of Monodisperse ZnSe Nanocrystals in a Non-Coordinating Solvent

The synthesis of ZnSe nanocrystals was carried in a similar fashion as described in Example 1 using $Zn(Ac)_2$ as the cation precursor, in which the selenium source for injections was an ODE solution of selenium-tributylphosphine (1:1.1 ratio). The Se-TBP or other selenium organophosphine compounds was prepared simply by dissolving Se in a desired amount of liquid organophosphine. The injection solution was further prepared by diluting the Se-phosphine solution with an adequate amount of ODE.

EXAMPLE 5

Preparation of Monodisperse InP Nanocrystals in a Non-Coordinating Solvent

In a typical synthesis, 0.1 mmol (0.03 g) of $In(Ac)_3$ (where Ac=acetate, $O_2CCH_3$) was mixed with a controlled amount of ligand, as described herein, and just under 5 g of ODE in a three-neck flask. The mixture, 5 g in total, was heated up to 100–120° C. to obtain an optically clear solution and pumped for two hours using a mechanical vacuum pump. The system was purged with argon three times, and then further heated up to 300° C. under an argon flow. A 0.05 mmol-sample of $P(TMS)_3$ (0.0125 g) was dissolved in ODE in a glovebox, 2 g in total, and injected into the hot reaction flask. While various ratios of indium to phosphorus reagents can be used, the best results for both single and multiple injection reactions were achieved by maintaining about a 2:1 indium to phosphorus molar ratio. After the injection, the temperature was dropped down to 270° C. for 1–2 h, for the growth of the InP nanocrystals. For multiple injections, successful secondary injections were performed dropwise at 250° C., by alternating 1 g injections of indium and phosphorus solutions in about half the molar concentration of the original solutions.

Aliquots of the reaction mixture were taken at different reaction times to monitor the progress of the reaction and crystallization. The resulting InP nanocrystals could be dissolved in typical non-polar solvents, and acetone and methanol were used to precipitate the nanocrystals from the ODE solution in order to remove starting materials and side products. No size sorting was performed on any of the samples used in the measurements. XRD and TEM measurements were also performed to characterize the crystallinity, size, and size distribution of the resulting crystals.

EXAMPLE 6

Preparation of Monodisperse InAs Nanocrystals in a Non-Coordinating Solvent

Figure 10:
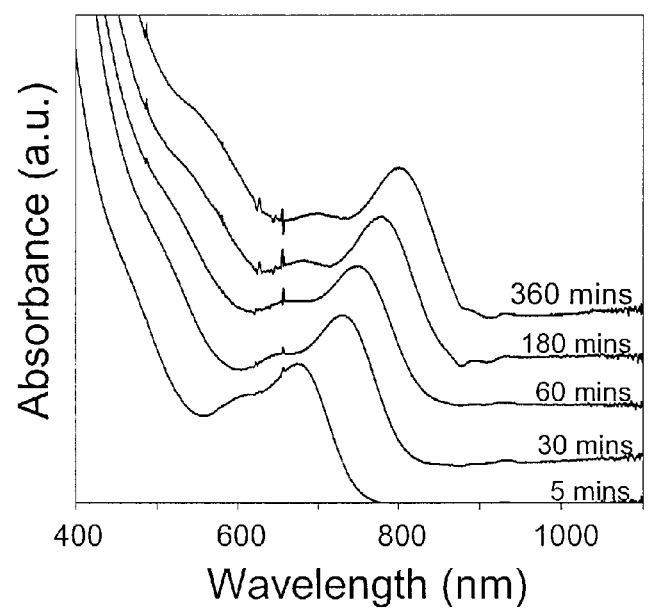
FIG. 10 demonstrates the temporal evolution of UV-Vis spectra of the as-prepared InAs nanocrystals grown in the non-coordinating solvent.

The synthesis of InAs nanocrystals was performed using 0.4 mmol (0.12 g) of $In(Ac)_3$, 1.2 mmol (0.34 g) of stearic acid ligand, less than 5 g of ODE, and a 0.05 mmol-sample of $As(TMS)_3$ (0.015 g) in a similar fashion as described in Example 4. The absorption spectra of the resulting InAs nanocrystals shown in FIG. 10 are very sharp, indicating that the size distribution of the samples is superiorly narrow.

EXAMPLE 7

Correlation of Reaction Time and Nanocrystal Size for Monodisperse CdS Nanocrystals Formed in a Non-Coordinating Solvent In order to demonstrate how the time of reaction is correlated with nanocrystal size in a single reaction, the following synthesis of CdS was performed, and aliquots of reaction mixture were sampled and examined as a functin of time. Table 1 presents the data obtained in this Example.

TABLE 1

Reaction time and average size (diameter, nm) for the formation of high quality CdS crystals formed in one reaction.

| Reaction Time (sec) | Average Nanocrystal Size (nm) |
|---|---|
| 16 | 2.2 |
| 24 | 2.8 |
| 33 | 3.0 |
| 46 | 3.5 |
| 60 | 3.9 |
| 81 | 4.2 |
| 100 | 4.3 |

Typically, CdO (0.10 mmol) and oleic acid (1.5 mmol) were added into 4 grams technical grade ODE (Tech ODE) in a three-neck flask. The mixture turned became optically clear around 200° C., and was continuously heated to 300° C. for the injection of a sulfur solution that contains 0.05 mmol of sulfur dissolved in 2 grams of Technical ODE. The resulting colorless optically clear solution was stable at room temperature and ready for the injection. After the swift injection of the sulfur solution, the temperature of the reaction mixture was allowed to cool down to 250° C. for the growth of the nanocrystals. Aliquots were taken at different time intervals and diluted by chloroform to monitor the reaction by UV-Vis absorption. The reaction was stopped by shutting down the heating. The reaction mixture was an optically clear, yellowish solution at room temperature. The nanocrystals synthesized by the present scheme, including the aliquots taken at different reaction times, were soluble in typical non-polar solvents such as hexanes, toluene and chloroform. No size sorting of any type was performed for the samples used for all of the measurements, including the size measurements disclosed herein. Size measurements were carried out as described in Example 1.

All of the publications or patents mentioned herein are hereby incorporated by reference in their entireties. The above examples are merely demonstrative of the present invention, and are not intended to limit the scope of the appended claims.

What is claimed is:

1. A method of synthesizing colloidal nanocrystals, comprising:
   a) combining a cation precursor, a ligand, and a non-coordinating solvent to form a cation-ligand complex; and
   b) admixing an anion precursor with the cation-ligand complex at a temperature sufficient to form nanocrystals.

2. The method of claim 1, wherein the cation precursor comprises a compound of a group II metal, a group III metal, a group IV metal, or a transition metal.

3. The method of claim 2, wherein the group II metal is selected from Zn, Cd, or Hg.

4. The method of claim 2, wherein the group III metal is selected from Al, Ga, or In.

5. The method of claim 2, wherein the group IV metal is selected from Ge, Sn or Pb.

6. The method of claim 1, wherein the cation precursor comprises a metal oxide, a metal carbonate, a metal bicarbonate, a metal sulfate, a metal sulfite, a metal phosphate, a metal phosphite, a metal halide, a metal carboxylate, a metal alkoxide, a metal thiolate, a metal amide, a metal imide, a metal alkyl, a metal aryl, a metal coordination complex, a metal solvate, or a metal salt.

7. The method of claim 1, wherein the ligand is selected from a fatty acid, an amine, a phosphine, a phosphine oxide, a phosphonic acid or combination thereof.

8. The method of claim 7, wherein the fatty acid is selected from decanoic acid, oleic acid, lauric acid, myristic acid, palmitic acid, or stearic acid.

9. The method of claim 1, wherein the non-coordinating solvent has a melting point less than about 25° C. and a boiling point greater than about 250° C.

10. The method of claim 1, wherein the non-coordinating solvent is octadecene.

11. The method of claim 1, wherein the anion precursor is selected from an element, a covalent compound, or an ionic compound.

12. The method of claim 1, wherein the anion precursor is selected from elemental S, elemental Se, elemental Te, selenium tributylphosphine, or tellurium tributylphosphine.

13. The method of claim 1, wherein the anion precursor is combined with a non-coordinating solvent, a ligand, or a combination thereof prior to admixing with the cation-ligand complex.

14. The method of claim 1, wherein the temperature sufficient to form nanocrystals is greater than about 200° C.

15. The method of claim 1, wherein nanocrystals of CdS are formed.

16. The method of claim 1, wherein nanocrystals of CdSe are formed.

17. The method of claim 1, wherein nanocrystals of CdTe are formed.

18. The method of claim 1, wherein nanocrystals of ZnSe are formed.

19. The method of claim 1, wherein nanocrystals of InP are formed.

20. The method of claim 1, wherein nanocrystals of InAs are formed.

21. The method of claim 1, wherein the mean diameter of the nanocrystals is from about 1 nm to about 6 nm.

22. A method of synthesizing colloidal nanocrystals, comprising:
   a) combining a cation precursor, a ligand, and a non-coordinating solvent to form a cation-ligand complex;
   b) admixing an anion precursor with the cation-ligand complex at a first temperature sufficient to induce reaction between the cation-ligand complex and the anion precursor; and
   c) adjusting the temperature of the mixture to a second temperature sufficient to form nanocrystals of the reaction product.

23. The method of claim 22, wherein the anion precursor is combined with a non-coordinating solvent, a ligand, or a combination thereof prior to admixing with the cation-ligand complex.

24. The method of claim 22, wherein the cation precursor is CdO, the ligand is oleic acid, the non-coordinating solvent is octadecene, and the anion precursor is elemental sulfur.

25. The method of claim 22, wherein the cation precursor is CdO, the ligand is oleic acid, the non-coordinating solvent is octadecene, and the anion precursor is selenium tributylphosphine.

26. The method of claim 22, wherein the cation precursor is CdO, the ligand is oleic acid, the non-coordinating solvent is octadecene, and the anion precursor is tellurium tributylphosphine.

27. The method of claim 22, wherein the cation precursor is $Zn(acetate)_2$, the ligand is oleic acid, the non-coordinating solvent is octadecene, and the anion precursor is elemental selenium tributylphosphine.

28. The method of claim 22, wherein the cation precursor is $In(acetate)_3$, the ligand is selected from myristic acid or palmitic acid, the non-coordinating solvent is octadecene, and the anion precursor is $P(SiMe_3)_3$.

29. The method of claim 22, wherein the cation precursor is $In(acetate)_3$, the ligand is selected from myristic acid or palmitic acid, the non-coordinating solvent is octadecene, and the anion precursor is $As(SiMe_3)_3$.

* * * * *